United States Patent
Crevatin et al.

(10) Patent No.: US 9,222,903 B2
(45) Date of Patent: Dec. 29, 2015

(54) METHOD OF DETERMINING THE SOFTENING- OR DROPPING POINT

(75) Inventors: Mario Crevatin, Winterthur (CH);
Markus Tuor, Niederglatt (CH);
Benjamin Arnold, Winterthur (CH);
Pascal Wildbolz, Bonaduz (CH); Daniel Scherrer, Zürich (CH)

(73) Assignee: Mettler-Toledo AG, Greifensee (CH)

(*) Notice: Subject to any disclaimer, the term of this patent is extended or adjusted under 35 U.S.C. 154(b) by 603 days.

(21) Appl. No.: 13/596,856

(22) Filed: Aug. 28, 2012

(65) Prior Publication Data

US 2013/0058374 A1 Mar. 7, 2013

(30) Foreign Application Priority Data

Sep. 5, 2011 (EP) ..................... 11179996

(51) Int. Cl.
| | | |
|---|---|---|
| G01K 11/00 | (2006.01) | |
| G01N 25/04 | (2006.01) | |
| G01N 33/42 | (2006.01) | |
| G01K 11/06 | (2006.01) | |

(52) U.S. Cl.
CPC ............. *G01N 25/04* (2013.01); *G01N 33/42* (2013.01); *G01K 11/06* (2013.01)

(58) Field of Classification Search
USPC .................................. 374/17, 161
See application file for complete search history.

(56) References Cited

U.S. PATENT DOCUMENTS

| | | |
|---|---|---|
| 426,160 A | 4/1890 | Woodard |
| 3,242,277 A | 3/1966 | Ceglia |
| 3,587,293 A | 6/1971 | Bowers et al. |
| 4,426,160 A | 1/1984 | Couderc |
| 5,100,111 A * | 3/1992 | Thomas ................. 266/88 |
| 6,536,944 B1 | 3/2003 | Archibald et al. |
| 8,092,078 B2 | 1/2012 | Bradley et al. |
| 2001/0028862 A1 * | 10/2001 | Iwata et al. ............ 422/56 |

(Continued)

FOREIGN PATENT DOCUMENTS

| | | |
|---|---|---|
| GB | 2464717 A | 4/2010 |
| JP | 58-62551 A | 4/1983 |

OTHER PUBLICATIONS

Bestimmung des Erweichungspunktes nach Mettler, Deutsche Norm, Apr. 1984, pp. 1-3, DIN 51 920, 5, Alleinverkauf der Normen durch Beuth Verlag GmbH, Berlin, Germany.

(Continued)

*Primary Examiner* — Lisa Caputo
*Assistant Examiner* — Nasir U Ahmed
(74) *Attorney, Agent, or Firm* — Standley Law Group LLP

(57) ABSTRACT

At least one of the softening point and the dropping point of a substance is determined with a measuring instrument that comprises a sample chamber (4), a temperature sensor (16), a heater device (11), a means for providing temperature/time target values, an image-recording means (5) and a controller unit (17) with a processor unit. The heater device heats the sample chamber, the temperature sensor measures the temperature in the sample chamber, and the image-recording means captures a visual image of the interior of the sample chamber. A method using the measuring instrument has at least the steps of determining the change over time of the sample as a function of temperature based on the recorded image/time data and actual temperature/time data, and of determining the dropping- or softening point of the sample based on the observed change over time as a function of temperature.

18 Claims, 4 Drawing Sheets

(56) References Cited

U.S. PATENT DOCUMENTS

2003/0118078 A1* 6/2003 Carlson ............... B01J 19/0046
374/160
2006/0245466 A1* 11/2006 Corbett ........................ 374/17

OTHER PUBLICATIONS

Drop Point, European Pharmacopoeia 6.0, pp. 33-34, 2.2.17, 2008.
Dropping Point, Sampling and Analysis of Commercial Fats and Oils, AOCS Official Method Cc 18-80, Reapproved 1997, Revised 2001, pp. 1-2.
Standard Test Method for Softening Point Resins (Mettler Cup and Ball Method), 2004, pp. 1-3, Designation: D 6090-99, ASTM Int'l, West Conshohocken, PA.
Standard Test Method for Softening Point of Asphalt and Pitch (Mettler Cup-and-Ball Method), 2005, pp. 1-6, Designation: D 3461-97 (Reapproved 2002), ASTM International, West Conshohocken, PA.
Standard Test Method for Dropping Point of Waxes, 2005, pp. 1-2, Designation: D 3954-94 (Reapproved 2004), ASTM International, West Conshohocken, PA.
Standard Test Method for Softening Point of Pitches (Mettler Softening Method), 2005, pp. 1-6, Designation: D 3104-99 (Reapproved 2005), ASTM International, West Conshohocken, PA.

* cited by examiner

METHOD OF DETERMINING THE SOFTENING- OR DROPPING POINT

CROSS-REFERENCE TO RELATED APPLICATIONS

This application is entitled to benefit of a right of priority under 35 USC §119 from European patent application 11179996.1, filed 5 Sep. 2011, the content of which is incorporated by reference as if fully recited herein.

TECHNICAL FIELD

The invention relates to a method for the determination of the softening- or dropping point of a substance and specifically concerns an automated method.

BACKGROUND

The determination of the softening- or dropping point is a commonly recognized procedure for the determination of characteristic properties of a material or a substance, specifically for substances that lack a sharply defined phase transition between the solid and the liquid state, making it impossible to determine an exact melting point.

The term "dropping point" means the temperature at which a substance begins to flow under given test conditions which are in many cases standardized. In the test, the substance is heated under controlled conditions until it changes from the solid to the liquid state. In the measurement, the temperature is registered at which a first drop detaches itself from the substance. The determination of the dropping point can be performed according to one of the common standards such as for example ASTM D3954, Ph. Eur. 2.2.17 (Pharmacopoeia Europaea), AOCS Cc 18-18 (American Oil Chemists' Society). In particular for polymers, raw polymers, waxes, polyolefins, paraffins, lubricant greases, organic powders, petroleum jellies, edible fats and oils and related substances, the dropping point is used for characterization as well as for quality control.

The softening point is a measured value used for the classification of, e.g., bitumina and bituminous substances. The softening point can be determined by means of a so-called ring-and-ball method as described for example in U.S. Pat. No. 3,242,277 A. For the determination of the value of the softening point, a steel ball is put on a layer of bitumen or a bitumen specimen positioned within a ring. In the course of the experiment, the material is uniformly heated, and the temperature at which the specimen has sagged downwards by 25.4±0.2 millimeters is recorded as the softening point. The softening point can also be determined by measuring the temperature at which an expanding drop has reached a certain length. The drop formation of the substance to be analyzed occurs as a result of heating. The softening point can be determined according to one of the common standards as for example ASTM D3104, D3461 and D6090 as well as DIN 51920. The determination of the softening point is likewise used for the quality control as well as for the characterization of bitumen, pitch, asphalt, resins, binding agents and related substances.

As an example, a device for the optical determination of the melting point is disclosed in GB 2464717 A, wherein a sample in a melting point capillary is visually observed during the heating of the sample and the data are evaluated for the determination of the melting point. The term "melting point" means the temperature at the phase transition from solid to liquid and lends itself well to visual observation, as a solid sample is normally opaque while a liquid sample is frequently transparent, so that the point at which an intensity maximum is reached can be essentially equated to the reaching of the melting point.

US 2009/0190626 A1 likewise discloses a device for the optical determination of the melting point and of other phase transitions of one or more substances that are arranged in depressions of a flat carrier. This device is less suitable to determine absolute values for the phase transitions, but is primarily intended for the determination of comparative values for different substances.

The sample or substance that is to be analyzed can be liquid or solid as well as in an intermediate state. For example, the substance can be described as liquid, solid, waxy, bituminous, viscous, or pulverous.

At present, the known state of the art offers primarily measuring instruments that allow either the determination of the softening point or the determination of the dropping point. In many cases, the determinations take place in measuring instruments with a heatable sample chamber. The substance to be analyzed is filled into a suitable sample receptacle which is set into the sample chamber in which the sample, i.e. the substance in the sample receptacle, is subsequently heated.

The reaching of the softening point is determined as the point at which the first drop of the substance has reached a given length and triggers for example an appropriately arranged light gate. The temperature at this time is registered as the softening point.

Another instrument for the optical determination of the softening point is disclosed in JP 58062551 A, wherein the shadow is measured that is cast by the drop and its length is evaluated.

The point at which the dropping point is reached is determined as the time at which the first drop falls off the sample. This event can likewise be detected by means of a light gate, and the corresponding temperature can be registered as the dropping point.

The measuring chambers of state-of-the-art measuring instruments are in most cases enclosed and not accessible for direct visual inspection. The enclosed design serves primarily to avoid thermal bridges, in particular cold bridges, reaching through a window and is chosen in the interest of a uniform heating of the sample. Other state-of-the-art measuring instruments use oil baths or water baths for the heating of the sample.

However, the determination of the softening point according to the conventional standards can only performed with substances whose behavior also conforms to those standards, i.e. substances which, when heated, will form a drop of the desired length. For example, no softening point can be determined for a substance even though a drop is formed by the heating, if the drop separates itself before it reaches the desired length or if the drop does not attain the prescribed length but hardens beforehand.

Consequently, the objective presents itself to provide a method as well as a measuring instrument which improves the reproducibility in the determination of the dropping- and/or softening point of substances conforming to the applicable standards and which, furthermore, makes it possible to also analyze substances whose behavior does not conform to the standards.

SUMMARY

This task is solved by a method for the determination of the softening- or dropping point of a substance with a measuring instrument. The measuring instrument comprises a sample chamber, a temperature sensor, a heater device, a means for providing target values of temperature vs. time, a means for recording images, in particular a means to capture digital images, and a controller unit with a processor unit. The heater device serves to heat the sample chamber in accordance with a given temperature profile such as the temperature/time target values. The temperature sensor serves to measure the temperature inside the sample chamber, and the image-recording means serves to acquire a visual image of the interior of the sample chamber.

The method according to the invention comprises several steps. First, a sample receptacle with a sample of the substance to be analyzed is provided and placed in the sample chamber. In addition, target values of temperature vs. time are provided. A given starting temperature is set in the sample chamber, and subsequently the sample chamber is heated according to the given target values of temperature vs. time. During the measurement phase, actual values of temperature vs. time are measured inside the sample chamber by means of the temperature sensor and, in addition, image/time data are acquired from the interior of the sample chamber with the image-recording means. Based on the recorded image/time data and actual-temperature/time data, a time profile of the change of the sample as a function of temperature can be determined. As a result of being heated in the sample chamber, the sample will develop at least one drop whose formation is recorded in the image/time data as the change of the sample over time. Based on the change of the sample over time as a function of temperature, the dropping- or softening point of the sample can be determined.

By analyzing the recorded actual temperature values and image/time data, the dropping- or softening point of the substance can be determined. Furthermore, the profile of actual temperature/time values and of the change of the sample determined from the image/time data allows conclusions to be drawn about other rheological parameters such as for example the viscosity of the substance.

The recording of the image further allows the substance to be optically monitored during the heating process, whereby the reproducibility of the measuring results can be improved, because measurement errors can easily be detected based on an atypical behavior of a sample. Such measuring errors can occur, for example, if the drop which develops in the determination of the softening point either detaches itself or stops growing before attaining the predetermined length, or if the drops which develop in the determination of the dropping point show a strong variation in size, shape or color, which can be a symptom that the sample is not heated evenly, or that the heat does not distribute itself uniformly in the sample. The reproducibility of the measurements can be improved by the capability to optically and/or visually observe the different behaviors of at least two identical samples and thus to detect differences between the actually identical samples.

Particularly in regard to the determination of the softening point, a further advantage lies in the capability for more exact measurements in substances that do not conform to the common standards. Among these are substances whose surface tension decreases in the softening, so that a drop detaches itself from the sample before it reaches the given length, or substances whose surface tension and/or internal tension is so high that no drop of the predetermined length will develop, but the drop will stop growing at a shorter length.

Preferably, the drop formation of the sample is observed from the recorded image/time data, so that measurement errors can be detected based on an irregular drop formation. Thus, irregularly formed drops can be rejected in the determination of the dropping- or softening point and, as has already been mentioned, the reproducibility of the determination is thereby improved.

The method according to the invention further comprises a step of adjusting the color balance and/or the white balance in order to adapt and/or adjust the color spectrum of means of image acquisition or image-recording means. For this purpose, an area of defined color, preferably white, can be arranged inside the sample chamber. Prior to loading the samples, an image of this area is taken and the image-recording means is adjusted so that the recorded image corresponds to a given color, for example R 100 G 100 B 100 of the RGB color scheme or of another defined color reference. The color- and/or white-balancing step makes it possible to record image/time data which are comparable to each other in particular based on the colors that are indicated in the data. For example in serial measurements, color differences between the samples can thus be detected, which is advantageous for the user because differences in color may be indicative of a different composition of the substance being analyzed or also of a breakdown of the substance.

With preference, the method according to the invention further comprises a brightness adjustment, which ensures that the image/time data are recorded under essentially identical brightness levels. This can bring an improvement in measurement reproducibility for samples of the same kind taken at different times. The brightness adjustment can be made in a variety of ways.

One possibility is to adjust the brightness of an adjustable light source which illuminates the sample chamber. The brightness is adjusted so that the image-recording means records image/time data at essentially identical illumination levels.

A further possibility is to adjust the exposure times in the recording of the image/time data, for example with a shutter which is part of the image-recording means and is kept open for a longer or shorter time interval in order to adjust the exposure time. Preferably, the shutter is an electronic shutter incorporated in the digital image-recording means.

Further, the brightness level in the image/time data can be adjusted mathematically. This makes it possible to ensure that all brightness values in the image are within a defined range, for example below 200, assuming that 0 represents the lowest and 255 represents the highest level of brightness.

As a further possibility, the calculated brightness adjustment can be defined for one or more specific substances. This is appropriate in particular for substances that are used as reference- and/or calibration substances. In this way, equal contrast conditions can be set for these substances, i.e. that the contrast between a given substance and the background is adapted to the given substance and, for example in repeated measurements, remains essentially the same. The attachment of a brightness level to a certain substance can be stored for example in a database in the controller unit.

In the course of the measurement, a change occurs in the sample over time as a result of the heating. In particular, this change can manifest itself as the drop formation which, depending on the substance to be analyzed, develops during the heating and detaches itself, or stretches out as a result of the heating and undergoes in particular a change in length. The temperature at which the drop breaks loose is referred to as the dropping point, while the temperature at which the growth of the drop passes a given length is referred to as the softening point. For most substances, it is possible to determine either a dropping point or a softening point. The change of the sample over time is determined from the image/time data. With a suitable image analysis, it is possible to determine the time and temperature at which a drop event has occurred, or the time and temperature at which the drop during its development attained the predetermined length.

To ensure that this determination can be made with the best possible reproducibility, the method further comprises a step of setting a reference point for a coordinate system or origin of coordinate axes. In this step, at least one predetermined point of the recorded image is set as the origin of the coordinates, and the determination of the change of the sample over time is performed in reference to this coordinate origin. A preferred point to select as the coordinate origin is for example the position of the sample chamber and in particular of an oven that borders on the sample chamber and partially surrounds the latter. Preferably, this position or another position that is fixed in the measuring instrument can be automatically detected based on the image/time data of the empty sample chamber, and can be set as the coordinate origin.

The image/time data and/or the temperature/time data can be recorded continuously, at predetermined time intervals, and/or at predetermined points in time.

Based on the change of the sample over time as a function of temperature, it is possible to determine for example the dropping point, the softening point and/or the viscosity as a material property and/or rheological property.

The actual temperature, an evaluation area, the time mark of the measurement, and/or a measurement scale for the length which is referenced in particular to the defined coordinate system origin can be shown in the representation of image/time data and can thus be correlated with the image/time data. This can be accomplished for example with a suitable physical arrangement of a temperature indicator, the evaluation area and/or a measurement scale in the measuring instrument, so that this information is registered in the recording of the image/time data. Preferably, the actual temperature, the evaluation area, the time mark or time stamp of the measurement, and/or the length measurement scale can be projected into the display of image/time data and thus visually tied together, so that the data are shown in logical juxtaposition to each other, in particular in the presentation of previously stored data. The combined display of image/time data, actual temperature, evaluation area, time mark of the measurement, and/or length measurement scale is user-friendly as well as advantageous in establishing the plausibility and traceability of the measurements. The time mark, i.e. the point in time at which the measurement took place, can be captured for example with a clock that is arranged with the measuring instrument and whose image is projected into the image/time data. The time mark can further be determined by way of the sampling rate, i.e. based on the predetermined time intervals at which the measurements are taken.

The measuring instrument further comprises a cooling device or cooperates with a cooling device, so that the sample in the sample chamber can also be cooled. This arrangement is advantageous if the solidification temperature of the substance under analysis is lower than the ambient room temperature, so that cooling is necessary prior to the determination of the dropping- or softening point. Preferably, substances of this kind are filled into pre-cooled sample receptacles and cooled to a temperature below their solidification temperature up to the start of the measurement or at least until the sample is placed into the sample chamber. The cooling device can be configured as a separate component or as a combined unit together with the heater device.

For sample receptacles the preferred choice are small metallic crucibles of a standardized shape as described for example in the standards cited hereinabove. The sample receptacles for the dropping point determination and the softening point determination have an inlet and an outlet and are distinguished from each other primarily by the diameter of the outlet through which the sample comes out in the form of a drop as it is being heated.

The image-recording means is configured as a means for the digital recording of images and can in particular be constituted by a CMOS camera, CCD (charge-coupled device) camera, any other state-of-the-art digital video recorder, or another suitable semiconductor-based image-acquisition device.

After a desired measurement process or measurement program has been set, specifically the starting temperature and the desired temperature/time target values, the act of placing the sample into the sample chamber can be detected, and the measurement of the temperature/time data and/or the recording of the image/time data can thus be started automatically by placing the sample in the sample chamber. Advantageously, one or more filled sample receptacles are arranged in a sample holder which carries a identification mark. In particular, the identification mark is designed to be recognized by way of the image/time data and/or the controller unit and thus triggers or starts the measurement.

The analysis of the measured image/time data and temperature/time data can be performed online, but the data can also be analyzed after the measurements have been completed, in particular as an off-line task.

The controller unit comprises at least one read/write memory in which the given temperature/time target values as well as the actually measured temperature/time values and the image/time data can be stored. Thus, the measurement results can be documented and can in addition be used again for one or more further analyses.

Furthermore, a program for performing the method is preferably stored in the controller unit.

The method according to the invention can be performed simultaneously on at least two substance samples that are in the sample chamber, whereby the measurement uncertainty can be reduced. The measuring instrument can for this purpose be equipped with a sample holder designed to hold two or more samples. The sample holder can be set into the measuring instrument together with the samples.

A measuring instrument that is operable to perform the method according to the invention comprises a sample chamber, a temperature sensor that measures the temperature in the sample chamber, a heater device, a means to provide temperature/time target values according to which the heater device heats the sample chamber, an image-recording means which records a visual image of the interior of the sample chamber, and a controller unit with a processor unit, wherein a sample set up in the sample chamber can be heated by means of the heater device in accordance with the given temperature/time target values. The actual temperature/time values can be measured with the temperature sensor, and the image/time data can be recorded with the image-recording means, so that the change over time taking place in the sample can be determined as a function of the temperature. The change over time of the sample includes the formation of at least one drop, which is represented in the image/time data. The change of the sample over time provides the basis for determining the dropping- or softening point of the sample.

To perform the method on two or more samples simultaneously, the measuring instrument can further be equipped with a sample holder with at least two seating positions for samples. Furthermore, the sample holder can include a holder means for each sample.

Advantageously, the sample holder also comprises a means of identification or identification mark whereby the characteristics of the sample holder can be recognized automatically, for example the number of samples that can be placed on it and/or whether the sample holder is of a type used for the determination of the dropping point or the softening point. After the sample holder has been set in place, the means of identification can be detected by way of the image-recording means and can be used to automatically start a given measurement process.

BRIEF DESCRIPTION

The method and a measuring instrument with the requisite capability to perform the method are described in more detail in the following drawings, wherein identical elements carry the same reference symbols, and wherein.

DETAILED DESCRIPTION

Figure 1:
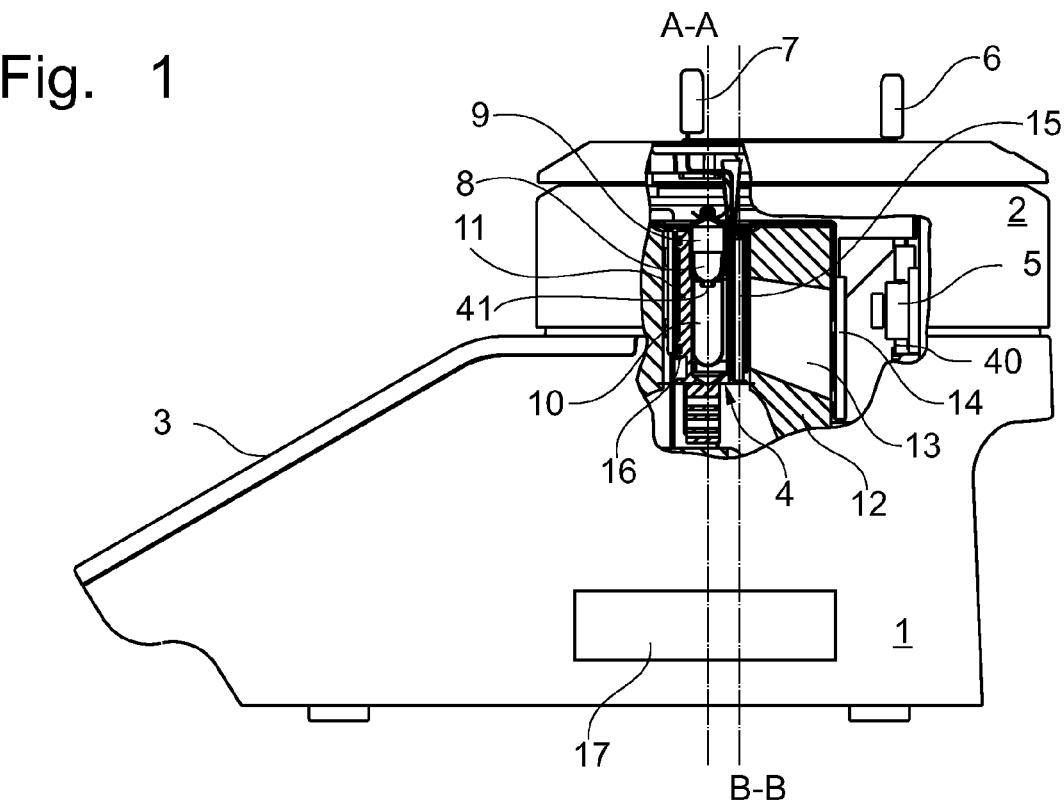
FIG. 1 represents a measuring instrument with a sample chamber as seen from the side in a partially sectional representation.
Figure 2:
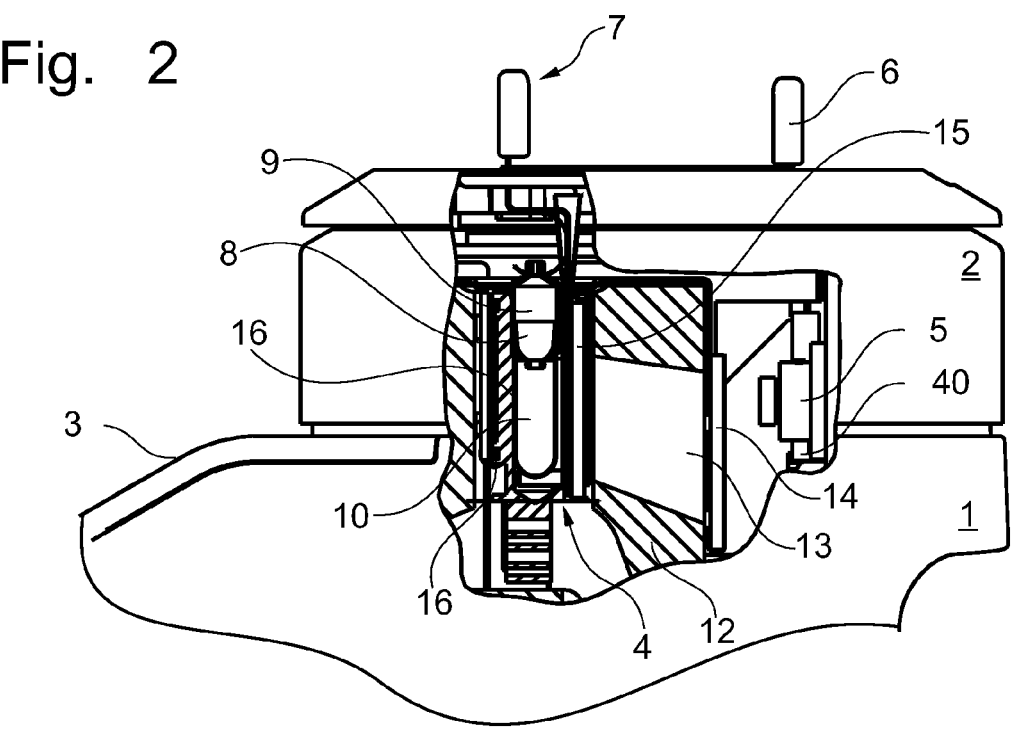
FIG. 2 shows a schematic detail representation of the sample chamber.

FIG. 1 shows a measuring instrument that is designed to perform the method, and FIG. 2 shows an enlarged detail view of a sample chamber in the measuring instrument. The following part of the description applies simultaneously to FIG. 1 and FIG. 2. The measuring instrument has a housing 1 and a housing part 2. Arranged in the housing 1 are among other components a controller unit 17 and other electronic components that are not explicitly shown here. In addition, the housing 1 has a slanted surface portion on one side where an operating- and/or display unit 3 is arranged. The housing part 2 is connected to the housing 1. The housing part 2 is equipped with a closure device 6 comprising a plate and a handle, which can be moved horizontally whereby an access to the sample chamber 4 can be opened or closed. Furthermore, arranged in the housing part 2 are a sample chamber 4, a digital image-recording means 5, and a suitable light source 40, specifically an LED lamp. As shown here, for carrying out the measurements a sample holder 7 can be arranged in the sample chamber 5. The sample holder 7 contains a sample receptacle 8 with a lid 9 placed on it and a collecting vessel 10 are arranged on the sample holder 7. The sample receptacle 8 has an outlet opening 41 through which at least one drop can come out when the sample is heated. The sample holder 7 can also be designed to accommodate a plurality of samples.

Arranged on at least one side of the sample chamber 4 is a heater device 11, preferably a flat panel heater, whereby the sample chamber 4, and thus a sample, can be heated in accordance with given temperature/time target values. In addition, a temperature sensor 16 can be arranged in the sample chamber 4 for the measurement of actual temperature/time values.

The side of the sample chamber 4 that faces towards the digital image-recording means 5 has a window 15 through which the digital image-recording means 5 can acquire image/time data from the interior of the sample chamber 4. Arranged between the digital image-recording means 5 and the window 15 is an insulation shield 12 of the sample chamber 4, in which a passage opening or cutout 13 is formed. The digital image-recording means 5 is protected towards the passage opening 13 by a further window panel 14.

Figure 3A:
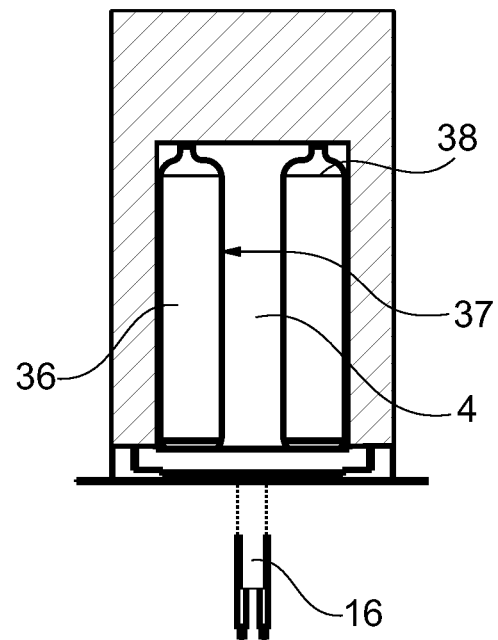
FIG. 3A shows a sectional view of the sample chamber without sample holder in the sectional plane indicated as A-A in FIG. 1.
Figure 3B:
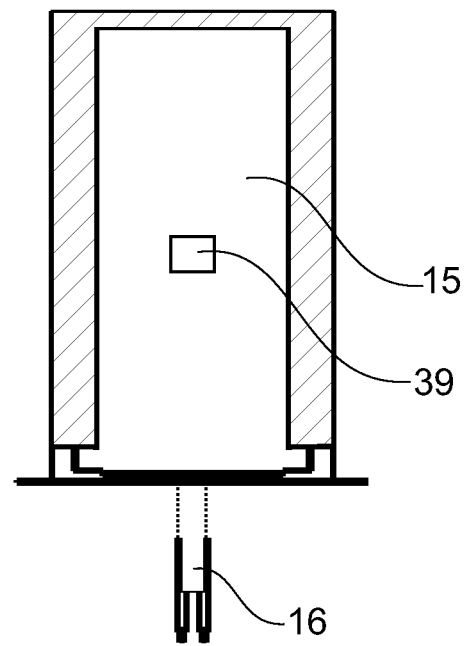
FIG. 3B shows a sectional view of the sample chamber without sample holder in the sectional plane indicated as B-B in FIG. 1.

FIGS. 3A and 3B both show a sectional view of the sample chamber 4 without sample holder, in the sectional planes indicated in FIG. 1 as A-A and B-B, respectively.

FIG. 3A shows two cavities 36 for two sample receptacles with covers and collecting vessels. Also shown is the connection for the temperature sensor 16 which, in this illustration, is arranged behind the drawing plane. In the method according to the invention, characteristic features of the empty sample chamber 4 are used for setting the point of origin for the coordinate system. As a reference for the horizontal position, one could use for example one or both of the inside contours 37 of the cavities 36 which, in an image of the empty sample chamber 4, appear as relatively sharp vertical silhouettes. As a vertical position reference, at least one of the upper abutments 38 is used against which the sample containers with lid and collecting vessel are seated in the installed position. The abutments 38 show up in the image data as sharply defined horizontal lines. The position of the shadow of at least one of the interior edges 37 is taken as the horizontal component of the origin of the coordinate grid, while the position of the shadow of the abutment 36 is taken as the vertical component, and the image detection according to the inventive method is accordingly referenced to this coordinate grid.

FIG. 3B shows a view of the sample chamber in the sectional plane indicated as B-B in FIG. 1 which, in reference to the digital image-recording means 5 (in FIG. 1) lies before the window 15. The window 15 carries a color reference area 39 of a given color, in this case a white rectangle, which is recorded and registered as a measured color in the inventive method in order to perform the white-balancing and/or color-balancing adjustment. Subsequently, the colors of the further images are digitally or mathematically adapted to the given value of the color reference area, for example RGB 100 100 100. The window 15 is transparent, but is represented as non-transparent in FIG. 3B in order to simplify the drawing.

Figure 4:
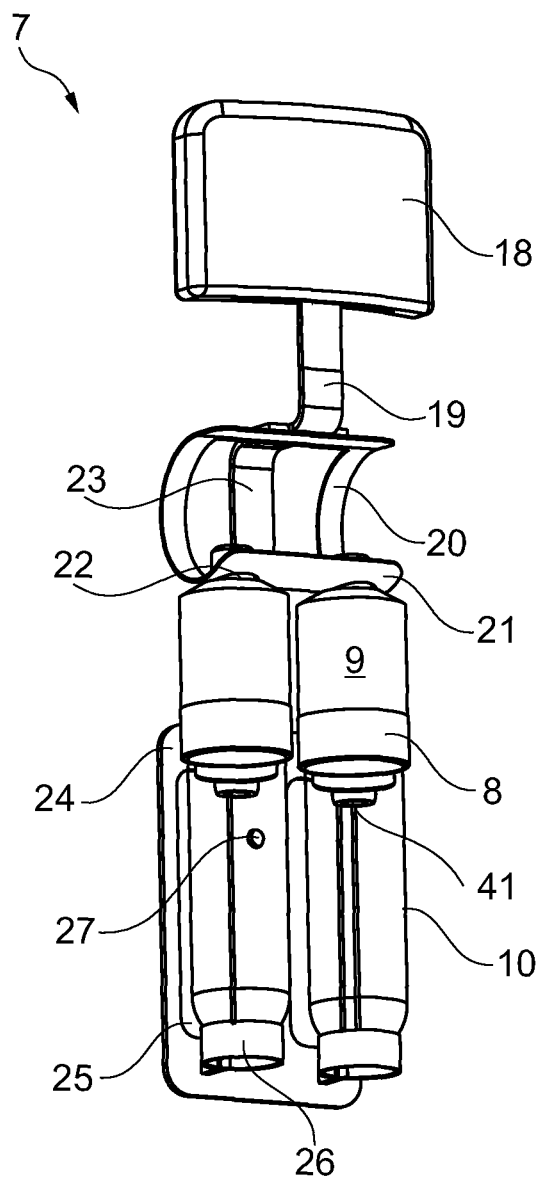
FIG. 4 shows a schematic three-dimensional representation of a sample holder.

FIG. 4 shows a schematic three-dimensional representation of a sample holder 7 for two samples. The substance that is to be analyzed can be filled into a sample receptacle 8 which is placed on a transparent collecting vessel 10. In addition, a lid 9 is set on the sample receptacle 8. The collecting vessel 10, the sample receptacle 8 and the lid 9 are set on top of each other, but are not firmly connected to each other in the illustrated example. When a sample which is arranged inside the sample receptacle 8 is exposed to heat, at least one drop develops which comes out of the sample receptacle 8 through an outlet opening 41 and expands into the collecting vessel 10.

The sample holder 7 comprises a handle 18 which is attached by way of a first connecting member 19 to a curved bracket consisting of two spring elements 20. The free ends of the spring elements 20 are tied together by a transverse connecting member 21 which has two cutouts or seats 22 for a portion of the lid 9. In addition, the first connecting member 19 extends into a further connecting member 23 which is directed away from the handle 18 and ends in a flat element 24 resembling a spatula. The flat element 24 has two vertical cutouts 25 and two ring-shaped holders 26 in which the collecting vessels 10 can be seated. The vertical cutouts 25 define the area of measurement that is captured by the digital image-recording means. In its inserted position in the measuring instrument, the sample holder 7 is oriented so that the sample receptacle 8 faces away from the digital image-recording means. As shown here, the collecting vessels 10 are transparent, so that the behavior of the sample over time can be captured by the digital image-recording means.

A means of identification or identification mark 27 can be arranged in the mid-section of the spatula-shaped element 24. The identification mark 27 is in this case configured as a hole. It allows the digital image-recording means to automatically detect the sample holder at the time of its insertion into the sample chamber. The identification mark 27 can vary in size, shape and/or position on the sample holder 7, so that different sample holders 7 can be distinguished from each other in the detection. Of course, the sample holder can also include several identification marks of the same or different types. Besides the hole that is shown in this example, it is also possible to use a plurality of holes, other distinctive marks as well as machine-readable codes such as barcodes or smart codes, or electronically detectable marks such as RFID tags.

Figure 5:
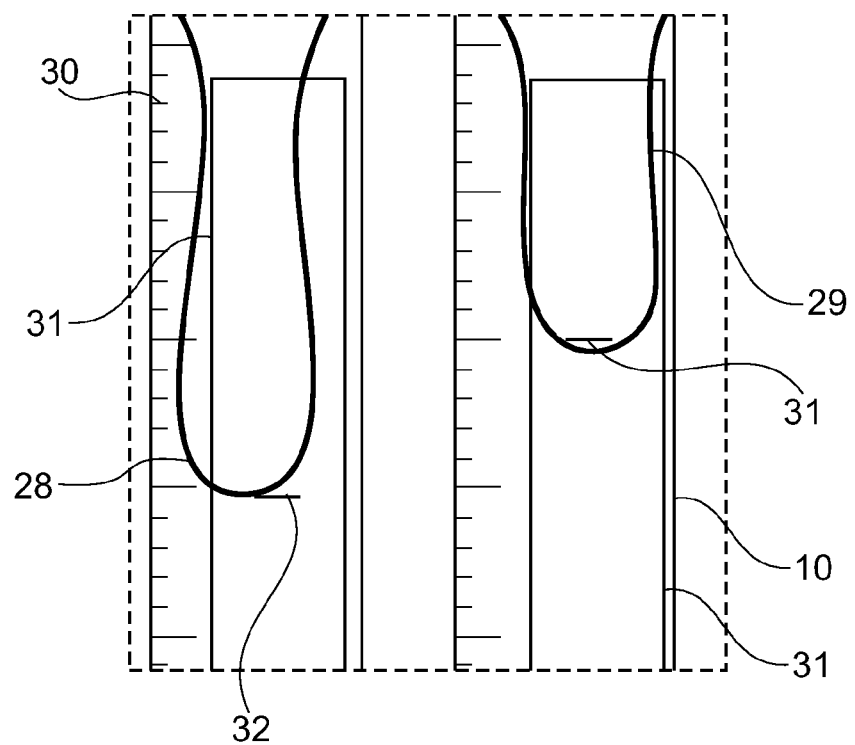
FIG. 5 shows a schematic representation of a recorded image of the interior of the sample chamber during a softening point determination.
Figure 6:
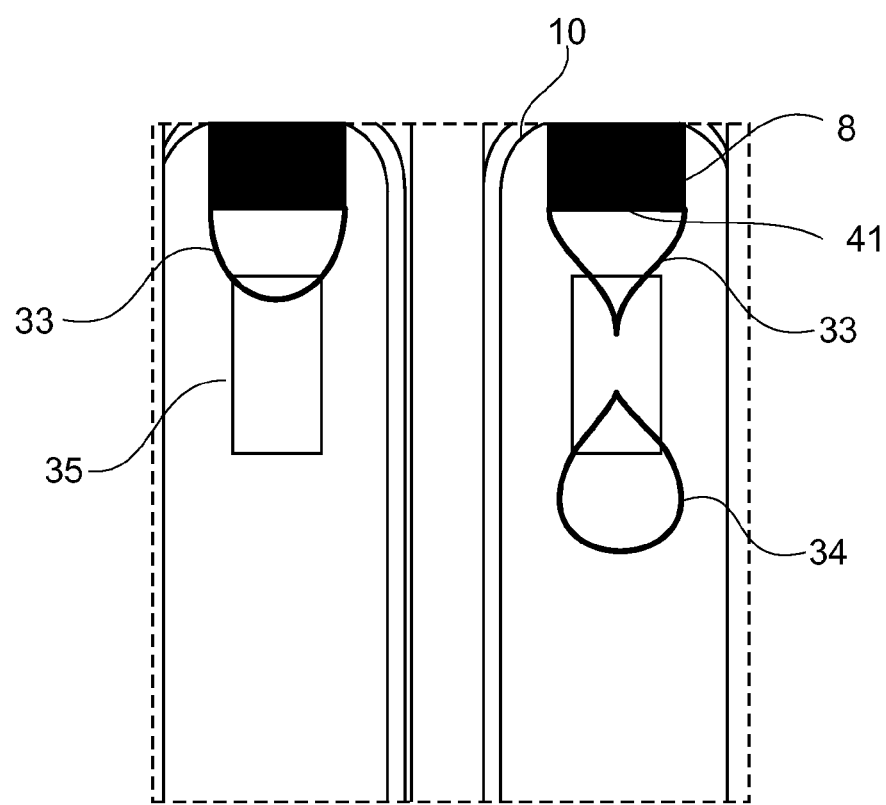
FIG. 6 shows a schematic representation of a recorded image of the interior of the sample chamber during a dropping point determination.

FIGS. 5 and 6 schematically illustrate recorded images of the interior of the sample chamber during a determination of the softening point or of the dropping point.

For the determination of the dropping point or the softening point in a practical example, a white-balancing or color-balancing adjustment is performed after switching on the instrument in order to adapt and/or adjust the color spectrum of the digital image-recording means. For this purpose, an area of defined color, preferably white, is arranged inside the sample chamber (see FIG. 3B). Prior to loading the samples, an image of this area is taken and the digital image-recording means is adjusted so that the recorded image corresponds to a given color, for example R 100 G 100 B 100 of the RGB color scheme. The color- and/or white-balancing step makes it possible to record image/time data which can be compared to each other in particular based on the colors that are indicated in the data. In addition, the color- and/or white-balancing step provides the possibility to compensate for changes of the light source, in this case an LED lamp, which is used to illuminate the sample chamber.

The next step is to determine an origin or zero point of a coordinate system, so that the determination can be performed with the best possible degree of reproducibility. In this step, at least one given point of the recorded image is defined as the origin of a coordinate system, and the determination of the change of the sample over time is referenced against this point of origin. A preferred choice of a fixed point for the definition of the origin of coordinates is for example the position of the sample chamber. The origin of coordinates should be defined based on a characteristic feature in the image which is easy to recognize and whose position can be determined in the horizontal as well as in the vertical direction (see FIG. 3A).

A brightness adjustment can be performed before or after the step of determining the origin of a coordinate system. Preferably, the origin for the coordinates is determined first. The brightness adjustment serves to ensure that the image/time data are recorded under essentially equal brightness conditions. In this way, the reproducibility of measurements taken for samples of the same kind at different times can be improved. The brightness adjustment can be performed with one of the methods described hereinabove. Preferably, the adjustment is made by adapting the exposure times.

Preferably, the color balance adjustment, the brightness adjustment as well as the determination of the origin of coordinates is performed automatically after the measuring instrument has been started. This process can be performed in the order of sequence as described here or in a different order. A program to perform these steps is stored in the controller unit, more specifically in the processor unit that is located inside the controller unit.

At this point, the instrument is ready to perform measurements, and at least one sample can be provided and preferably filled into a sample receptacle that is suitable for the type of measurement to be performed. The sample receptacle can then be set into a sample holder, the specifics of which have been described in the context of FIG. 4. In many cases, two or more samples are measured simultaneously.

Prior to setting the sample holder into the measuring instrument, the measurement- and sample parameters can be determined by the user and entered by way of the display- and/or operating unit. These parameters comprise for example information about the substance, the temperature/time target values to be set, the starting temperature, and further items of information that are of relevance to the user.

After the sample holder with the at least one sample has been set into the measuring instrument, another brightness adjustment can be performed specifically for the respective sample, so that comparable brightness conditions are created for the substance to be analyzed, i.e. that the contrast between substance and background is essentially the same between samples of the same substance. The assignment of a brightness value to a given substance can be stored for example in a database in the controller unit. For substances that are used as references for adjustment and calibration of the instrument, these brightness values can either be furnished already by the manufacturer of the instrument, or they can be determined by the user. The determination by the user is particularly appropriate in the case of serial measurements or for measurements in the area of quality control, where in many cases substances of the same or very similar substances are measured.

The start of the measurement can be triggered by the user, or it can be started automatically through the detection of an identification mark on the sample holder. The measurement comprises the selection of the measurement method, i.e. whether the dropping point or the softening point is to be measured, the setting of the desired starting temperature, and the heating of the sample chamber to the selected starting temperature. Subsequently, the heater device heats up the sample chamber, and thus the sample, in accordance with the given temperature/time target values. As the sample is heated up, a drop is formed which expands through the outlet opening of the sample receptacle into the collecting vessel. Simultaneously, temperature/time data as well as image/time data are recorded at predetermined points in time or continuously and are preferably stored in memory.

Based on these data, the change of the sample over time can be determined. This determination is made nearly in real time, and/or it can be made later based on the recorded and stored data.

From the observation of the change of the sample over time, the first dropping event, i.e. the point of separation of the first drop from the sample, is determined and the associated temperature is recorded as the dropping point. Alternatively, the point at which the first drop reaches a predetermined length is determined and the associated temperature at that point in time is recorded as the softening point.

Additionally, in a further step, one or more rheological properties of the sample can be determined from the change of the sample over time. The analysis of the image/time data alone can already provide the user with information about the temperature-dependent rheological behavior of the substance that is to be analyzed.

FIG. 5 schematically illustrates a typical recorded image for the determination of the softening point. The image shows the interior of the sample chamber, specifically the area in which the collecting vessels are arranged. Two samples 28, 29 are present in the sample chamber. The samples have expanded as a result of heating and each sample has formed a drop. Superimposed on the image of the drop is a measurement scale 30, and a measurement range 31 is indicated by the superimposed frame. Based on the recorded image/time data, the length of the drop is determined and, in addition, indicated to the user by a horizontal indicator mark 32 which indicates the bottom end of the drop. As soon as the drop has attained a predetermined length, the associated temperature is registered as the softening point.

Analogously, FIG. 6 schematically illustrates a recorded image of the interior of the sample chamber during a dropping point determination. The image again shows the area captured by the image-recording means, which comprises the collecting vessels. The recording represents the point in time at which the dropping point is reached. The dropping point is registered by digitally evaluating the image of the observation window 35 and registering the breaking-off of a drop 34 from the substance 33. The associated temperature is recorded as the dropping point.

In addition, it is also possible to determine a rheological property of the substance, in particular the viscosity, from the recorded actual temperature/time data and the image/time data. This can be accomplished for example by measuring and analyzing the frequency at which the drops are formed.

Although the invention has been described through the presentation of specific examples of embodiments, it will be evident to the reader that numerous further variant embodiments could be developed from the teachings of the present invention, for example by combining the features of the individual examples with each other and/or be interchanging individual functional units between the embodiments described herein.

What is claimed is:

1. A method of determining, for a sample of a substance, a drop-forming property of the substance, the method comprising the steps of:
    setting the sample into a sample receptacle of a measuring instrument, the measuring instrument comprising, in addition to the sample receptacle:
       a sample holder comprising a seat in which the sample receptacle is received;
       a sample chamber, sized and adapted to receive the sample holder;
       a means for providing temperature/time target values;
       a heater device, arranged to heat the sample chamber according to the temperature/time target values;
       a temperature sensor, arranged to measure a temperature in the sample chamber;
       an image-recording means, arranged to capture a visual image of the sample in the sample chamber; and
       a controller unit with a processor unit;
       wherein a first configuration of the sample receptacle is adapted for determining a dropping point as the drop-forming property and a second configuration of the sample receptacle is adapted for determining a softening point as the drop-forming property;
    setting the sample chamber to a predetermined starting temperature and heating the sample chamber with the heater device, using a set of the predetermined temperature/time target values based upon the drop-forming property being determined;
    measuring, with the temperature sensor, the actual temperature/time values in the sample chamber and capturing image/time data from an interior of the sample chamber with the image-recording means;
    determining, in the processor unit, and using a program stored as instruction sets in non-volatile memory thereof, the change of the sample over time as a function of the temperature based on the recorded image/time data and actual temperature/time data, where the instruction set used is based upon the configuration of the sample receptacle; and
    determining, in the processor unit, the selected drop-forming property of the sample.

2. The method of claim 1, wherein:
in the step of determining change of the sample over time, the formation of the at least one drop is determined from the image/time data, whereby measurement errors are determined or detected from an irregular formation of the drop.

3. The method of claim 2, wherein:
the measuring and capturing step comprises at least one of a color-balance adjustment and a white-balance adjustment, wherein the color spectrum rendered by the image-recording means is adjusted using a color reference area of a defined color which is arranged in the sample chamber.

4. The method of claim 1, further comprising:
adjusting the brightness for the recording of the image/time data.

5. The method of claim 4, wherein:
the brightness adjusting step further comprises a substance-specific contrast equalization between a given value for the substance and the actual value.

6. The method of claim 4, wherein:
the brightness adjusting step is achieved through at least one of:
    adjusting the brightness of an adjustable light source;
    adjusting an exposure time of the image-recording means; and
    adjusting of the recorded digital image/time data, using a program, stored as instruction sets stored in non-volatile memory of the processor unit.

7. The method of claim 6, wherein:
the brightness adjusting step further comprises a substep of equalizing a substance-specific contrast between a given value for the substance and the actual value.

8. The method of claim 1, further comprising the step of:
determining a point of origin of a coordinate system within the sample chamber.

9. The method of claim 1, wherein:
the recorded image/time data include information regarding the actual temperature in the sample chamber, the change in length, and/or the drop-formation behavior of the substance by comprising:
    a temperature indication;
    an area of evaluation; and
    a length measurement scale.

10. The method of claim 1, wherein:
the measuring instrument further comprises a cooling device, arranged to cool the sample chamber.

11. The method of claim 1, wherein:
the measuring and capturing step is achieved by recording the image/time data and the temperature/time data in predetermined time intervals.

12. The method of claim 1, wherein:
the measuring and capturing step starts automatically when the sample is set into the sample chamber.

13. The method of claim 1, wherein:
a program, stored as instruction sets stored in non-volatile memory of the processor unit, is operable to automatically detect from the image/time data when at least a given length of the sample is exceeded or when a drop-formation event has occurred, and to indicate the associated actual temperature to a user.

14. The method of claim 1, wherein:
the step of measuring and capturing comprises the step of recording the image/time data and the temperature/time data in a read/write memory of the processor unit.

15. The method of claim 1, wherein:
the step of setting the sample in the sample chamber is achieved by placing the sample, contained in a sample receptacle, in the sample chamber.

16. An instrument for determining, for a sample of a substance, a drop-forming property, the instrument comprising:
a sample holder, comprising:
in a first configuration, a sample receptacle adapted for determining a dropping point of the sample as the drop-forming property;
in a second configuration, a sample receptacle adapted for determining a softening point of the sample as the drop-forming property; and
a seat in which the sample receptacle, of either configuration, is received;
a sample chamber, sized and adapted to receive the sample holder;
a means for providing predetermined temperature/time target values;
a heater device, arranged to heat the sample chamber in accordance with the predetermined temperature/time target values;
a temperature sensor, arranged to measure the actual temperature/time values in the sample chamber;
an image-recording means, arranged to capture a visual image of the interior of the sample chamber and to record image/time data; and
a controller unit with a processor unit that has a program stored in instruction sets in non-volatile memory, such that, in the first configuration of the sample holder, the image/time and the temperature/time data are used to determine the dropping point of the substance and, in the second configuration of the sample holder, the image/time and temperature/time data are used to determine the softening point of the substance.

17. The instrument of claim 16, wherein:
the sample holder further comprises at least two sample receptacles and at least two seats for receiving the sample receptacles.

18. The instrument of claim 17, wherein:
the sample holder further comprises a lid for each sample receptacle.

* * * * *